(12) United States Patent
Pearson et al.

(10) Patent No.: US 6,288,106 B1
(45) Date of Patent: Sep. 11, 2001

(54) PROCESSES FOR THE SYNTHESIS AND USE OF VARIOUS α-LIPOIC ACID COMPLEXES

(75) Inventors: Don C. Pearson, Lakewood, WA (US); Kenneth T. Richardson, Anchorage, AK (US)

(73) Assignee: ChronoRX, LLC, Anchorage, AK (US)

( * ) Notice: Subject to any disclaimer, the term of this patent is extended or adjusted under 35 U.S.C. 154(b) by 0 days.

(21) Appl. No.: 09/564,074

(22) Filed: May 3, 2000

Related U.S. Application Data

(60) Provisional application No. 60/136,020, filed on May 25, 1999.

(51) Int. Cl.$^7$ .................. A61K 31/385; C07D 339/02
(52) U.S. Cl. ................................ 514/440; 549/39
(58) Field of Search ................. 549/39; 514/440

(56) References Cited

U.S. PATENT DOCUMENTS

| | | | | |
|---|---|---|---|---|
| 5,569,670 | * | 10/1996 | Weischer et al. | 514/440 |
| 5,925,668 | * | 7/1999 | Biewenga et al. | 514/440 |
| 5,965,618 | * | 10/1999 | Perricone | 514/558 |
| 5,990,152 | * | 11/1999 | Hettche et al. | 514/440 |
| 5,990,153 | * | 11/1999 | Wood et al. | 514/440 |
| 6,046,228 | * | 4/2000 | Rice et al. | 514/441 |
| 6,117,899 | * | 9/2000 | Wessel et al. | 514/440 |

OTHER PUBLICATIONS

Seyerl, Joachim, CA 133:286430, 2000.*
Hasunuma, Kyotaro, CA 108:26828, 1988.*
Reed et al, CA 111:170547, 1989.*
Baumgartner et al, CA 126:86390, 1996.*
Biewenga et al, CA 127:242651, 1997.*
Wood et al, CA 131:356109, 1999.*
Bettger, W. J. (1993). "Zinc and selenium, site–specific versus general antioxidation." *Canadian Journal of Physiology & Pharmacology* 71(9): 721–4.
Bierhaus, A., S. Chevion, et al. (1997). "Advanced glycation end product–induced activation of NF–kappaB is suppressed by alpha–lipoic acid in cultured endothelial cells." *Diabetes* 46(9): 1481–90.
Cameron, N. E., M. A. Cotter, et al. (1998). "Effects of alpha–lipoic acid on neurovascular function in diabetic rats: interaction with essential fatty acids." *Diabetologia* 41(4):390–9.
Clausen, J. (1984). "Demential syndromes and the lipid metabolism." *Acta Neurol Scand* 70(5):345–55.
Conlon, B. J., J. M. Aran, et al. (1999). "Attenuation of aminoglycoside–induced cochlear damage with the metabolic antioxidant alpha–lipoic acid [In Process Citation]." *Hear Res* 128(1–2):40–4.

Cooke, J. P. (1996). "Role of nitric oxide in progression and regression of atherosclerosis." *West J Med* 164(5):419–24.
Haefliger, I. O., A. Zschauer, et al. (1994). "Relaxation of retinal pericyte contractile tone through the nitric oxide–cyclic guanosine monophosphate pathway." *Investigative Ophthalmology & Visual Science* 35(3): 991–7.
Hagen, T. M., R. T. Ingersoll, et al. (1999). "(R)–alpha–lipoic acid–supplemented old rats have improved mitochondrial function, decreased oxidative damage, and increased metabolic rate." *Faseb J* 13(2): 411–8.
Kotler, M., C. Rodriguez, et al. (1998). "Melatonin increases gene expression for antioxidant enzymes in rat brain cortex." *J Pineal Res* 24(2): 83–9.
Kunt, T., T. Forst, et al. (1999). "alpha–Lipoic acid reduces expression of vascular cell adhesion molecule– 1 and endothelial adhesion of human monocytes after stimulation with advanced glycation end products." *Clin Sci (Colch)* 96(1): 75–82.
Luscher, T. F., Z. Yang, et al. (1992). "Endothelin–induced vasoconstriction and calcium antagonists." *Journal of Human Hypertension* 6 (Suppl 2): S3–8.
McCully, K. S. (1994). "Chemical pathology of homocysteine. III. Cellular function and aging." *Ann Clin Lab Sci* 24(2): 134–52.
Nathanson, J. A. and M. McKee (1995). "Alterations of ocular nitric oxide synthase in human glaucoma." *Invest Ophthalmol Vis Sci* 36(9): 1774–84.
Reaven, G.M. (1994). "Syndrome X: 6 years later." *J Intern Med* Suppl 736: 13–22.
Riley, M. V., C. A. Schwartz, et al. (1986). "Interactions of ascorbate and H2O2: implications for in vitro studies of lens and cornea." *Curr Eye Res* 5(3): 207–16.
Schempp, H. and E. F. Elstner (1998). Free Radicals in the Pathogenesis of Ocular Diseases. *Nitric oxide and endothelin in the pathogenesis of glaucoma*. I. O. Haefliger and J. Flammer. Philadelphia, Lippincott–Raven: 112–135.
Tezel, G., M. A. Kass, et al. (1997). "Plasma and aqueous humor endothelin levels in primary open–angle glaucoma." *J Glaucoma* 6(2): 83–9.

* cited by examiner

Primary Examiner—Deborah C. Lambkin
(74) Attorney, Agent, or Firm—Townsend and Townsend and Crew LLP

(57) ABSTRACT

This invention is in the fields of pharmacology and biochemistry. It relates to processes for the synthesis of certain complexes of α-lipoic acid and the nutritional or therapeutic use of these and other related individual or complexed antioxidant, proglutathione molecules. Therapeutic uses for these molecules and complexes in the clinical management of conditions and functions associated with chronic glaucoma, insulin resistance, macular degeneration, lenticular cataract, neurodegenerative diseases, essential hypertension, atherosclerosis and vasoconstriction are described in particular.

15 Claims, No Drawings

PROCESSES FOR THE SYNTHESIS AND USE OF VARIOUS α-LIPOIC ACID COMPLEXES

CROSS REFERENCE TO RELATED APPLICATION

This application is related to U.S. Provisional Patent Application No. 60/136,020, filed May 25, 1999, and claims all benefits legally available therefrom. Provisional Patent Application No. 60/136,020 is hereby incorporated by reference for all purposes capable of being served thereby.

BACKGROUND OF THE INVENTION

This invention is in the fields of pharmacology and biochemistry. It relates to processes for the synthesis of certain complexes of α-lipoic acid and the nutritional or therapeutic use of these and other related individual or complexed antioxidant, proglutathione molecules. Clinical uses for these molecules and complexes in the management of chronic open angle glaucoma, hearing loss, macular degeneration, lenticular cataract, insulin resistance, diabetic retinopathy, coronary artery disease, Parkinson's disease, Alzheimer's disease, various neurodegenerative diseases and vasoconstriction are described in particular.

I. Clinical Review

A. Chronic Glaucoma

The eye is maintained in a homeostatic shape by a relatively stable intraocular pressure (IOP), which varies within a reasonably narrow range so long as the intraocular production of aqueous fluid remains equal to its exit from the eye.

The optic nerve head can tolerate relatively high levels of IOP if the availability of oxygen from posterior ciliary arteries and optic nerve head arterioles remains adequate. However, if the intraocular (extravascular) pressure is higher than the perfusion (intravascular) pressure driving oxygen through the arteriole into the surrounding tissues, decreasing amounts of oxygen will reach the optic nerve head and nerve disability will result.

Similarly if nerve head arterioles are unable to provide sufficient volumes of blood to the optic nerve, dysfunction will follow. These arteriolar vascular flow deficiencies may occur because of: vasoconstriction secondary to generalized or localized microvascular dysregulation, arteriolar muscular hypertrophy (perhaps as a result of chronic spasm), atherosclerotic luminal reduction, changes in the viscosity or laminar flow patterns of the arterial blood or in either essential or iatrogenic systemic hypotension.

Glaucoma in various guises affects a large segment of the public. It is estimated that 2% to 2.5% of the population over the age of 40 has chronic open angle glaucoma (COAG). This is the most common form of glaucoma.

Because optic nerve damage occurs in patients with chronically elevated IOP, present treatments concentrate on reducing this single, objective finding by a variety of modalities: topical eye drops, oral medications, intravenous medications, surgical procedures, laser phototherapy, etc. All of these focus upon the reduction of pressure inside the eye and rely upon this pressure reduction to prevent optic nerve damage. For many patients this approach is effective. However, the effectiveness of each of these treatments runs from total ineffectiveness, progressive optic atrophy and eventual blindness, to an arrest of the disease, complete cessation or prevention of further optic nerve failure and preservation of vision.

Factors other than IOP levels influence the clinical outcome for many glaucoma patients. Attention is now focusing upon two alternatives: a) hypovascularity of the optic nerve head and loss of the vascular integrity of the optic nerve resulting in glial collapse, ganglion cell apoptosis and progressive neural atrophy with visual loss; b) hypoxia-induced free radical interference with retrograde axoplasmic flow within the optical neural axons.

(i) Ocular Microvascular Regulation

A balanced biochemistry of nitric oxide (NO) and endothelin-1 (ET-1) mediates local optical blood flow and many facets of systemic vascular autoregulation.

NO is a highly soluble gas formed within endothelial cells by the action of the constitutive enzyme nitric oxide synthetase (cNOS). NO activates guanylate cyclase and increases guanosine monophosphate (cGMP) within the vascular musculature. cGMP produces relaxation and dilatation of vessels. It also has more generalized smooth muscle relaxing abilities; in this regard it relaxes the contractile trabecular elements of the eye, increases aqueous outflow and reduces IOP. Levels of NO in the trabecular region of eyes of glaucoma patients are lower than in the eyes of non-glaucoma patients. Aging and atherosclerotic dysfunction of the vascular endothelium reduce its ability to produce NO because of reduced local levels of cNOS.

ET-1 is also formed within and secreted by endothelial cells. ET-1 reacts with local receptors on smooth muscle cells to produce a powerful and long-lasting vasoconstriction. ET-1 is particularly released by aged or unhealthy endothelial cells, e.g., in the presence of atherosclerosis, in the presence of local collections of endothelial leukocytes or platelets, and during periods of significantly reduced vascular flow and decreased blood fluidity, etc. The smooth muscle contraction produced by ET-1 strongly opposes the relaxation properties of NO and trabecular contraction is stimulated, resistance to aqueous outflow is increased and IOP increases. Aqueous levels of ET-1 are elevated in glaucomatous eyes. Experimentally-induced elevations of aqueous ET-1 levels produce optic nerve collapse.

This balance between NO and ET-1 mediates the autoregulation of blood flow within the optic nerve and throughout the peripheral circulation.

Exposure of some hypertensive glaucoma patients to therapeutic amounts of calcium channel blockers has resulted in a serendipitous improvement of their glaucomatous visual fields. Vascular endothelial production of ET-1 is dependent upon cytosolic calcium ($Ca^{2+}$) influx via transmembrane calcium channels. Calcium channel blockade reduces this $Ca^{2+}$ influx and reduces the production of ET-1. A reduction of IOP has also been observed as a side effect in glaucoma patients using calcium channel blockers for systemic hypertension. However, prescribing therapeutic doses of calcium channel blockers to non-hypertensive glaucoma patients subjects the optic nerve to a risk of hypoxia secondary to iatrogenic hypotension and severely disrupts inherent transmembrane calcium modulation.

(ii) Ocular Vascular Disease

A balanced biochemistry of nitric oxide (NO) and endothelin-1 (ET-1) mediates local optical blood flow and many facets of systemic vascular autoregulation.

NO is a highly soluble gas formed within endothelial cells by the action of the constitutive enzyme nitric oxide synthetase (cNOS). NO activates guanylate cyclase and increases guanosine monophosphate (cGMP) within the vascular musculature. cGMP produces relaxation and dilatation of vessels. It also has more generalized smooth muscle relaxing abilities; in this regard it relaxes the contractile trabecular elements of the eye, increases aqueous outflow and reduces IOP. Levels of NO in the trabecular region of eyes of glaucoma patients are lower than in the eyes of non-glaucoma patients. Aging and atherosclerotic dysfunction of the vascular endothelium reduce its ability to produce NO because of reduced local levels of cNOS.

ET-1 is also formed within and secreted by endothelial cells. ET-1 reacts with local receptors on smooth muscle cells to produce a powerful and long-lasting vasoconstriction. ET-1 is particularly released by aged or unhealthy endothelial cells, e.g., in the presence of atherosclerosis, in the presence of local collections of endothelial leukocytes or platelets, and during periods of significantly reduced vascular flow and decreased blood fluidity, etc. The smooth muscle contraction produced by ET-1 strongly opposes the relaxation properties of NO and trabecular contraction is stimulated, resistance to aqueous outflow is increased and IOP increases. Aqueous levels of ET-1 are elevated in glaucomatous eyes. Experimentally-induced elevations of aqueous ET-1 levels produce optic nerve collapse.

This balance between NO and ET-1 mediates the auto-regulation of blood flow within the optic nerve and throughout the peripheral circulation.

Exposure of some hypertensive glaucoma patients to therapeutic amounts of calcium channel blockers has resulted in a serendipitous improvement of their glaucomatous visual fields. Vascular endothelial production of ET-1 is dependent upon cytosolic calcium ($Ca^{2+}$) influx via transmembrane calcium channels. Calcium channel blockade reduces this $Ca^{2+}$ influx and reduces the production of ET-1. A reduction of IOP has also been observed as a side effect in glaucoma patients using calcium channel blockers for systemic hypertension. However, prescribing therapeutic doses of calcium channel blockers to non-hypertensive glaucoma patients subjects the optic nerve to a risk of hypoxia secondary to iatrogenic hypotension and severely disrupts inherent transmembrane calcium modulation.

(iii) Glaucoma—Biochemistry of Present Treatment

Current non-surgical treatments of COAG are based upon a limited number of biochemical approaches and focus exclusively upon reducing IOP:

a. Enzyme poisons—these are most frequently tablets of carbonic anhydrase inhibitors, which inhibit the production of aqueous humor. Besides the development of renal stones, potassium loss is a constant clinical concern. Topical forms of this group have appeared as eye drops. However, because carbonic anhydrase activity is also present in the cytoplasm of corneal endothelial cells the long-term corneal effects of this form of these medications are unknown. To avoid systemic reactions, patients with sulfonamide allergies should not use these drugs.

b. Parasympathomimetics—pilocarpine-containing eye drops are widely prescribed and act by causing pupillary constriction. Miosis causes lacunae in the trabeculum to enlarge; thus, mechanical resistance to aqueous outflow is reduced. Frequent side effects include headache from iris spasm, decreased night vision from miosis and blurred vision in myopes especially.

c. Beta blocking agents—these drugs block the beta-adrenergic sympathetic rete responsible for increased vascular flow to the ciliary processes and consequently reduce the production of aqueous humor. They also increase aqueous outflow through the trabeculum. These agents must be used with great caution in patients with low blood pressure (orthostatic hypotension), sinus bradycardia or second/third degree heart block (severe bradycardia), obstructive pulmonary disease or bronchial asthma (acute bronchospasm) and diabetes (masking of hypoglycemia. They result in impotency in a significant number of men. There is contested evidence that ocular beta blocking agents generally reduce blood flow to the posterior segment of the eye.

d. Topical prostaglandin analogs—this very new group of anti-inflammatory eye drops presumably reduces IOP by widening the inter-trabecular space and, perhaps, by reducing trabecular platelet aggregation. Their use is associated with progressive and possibly permanent change in iris color to brown and some embryocidal outcomes in laboratory animals. Women of reproductive age and nursing women should avoid their use.

All of these treatment modes have significant and unavoidable, potential or demonstrable, local or systemic side effects or toxicities that directly contraindicate their use, reduce patient compliance or are worrisomely interactive with other systemic pharmaceuticals.

B. Hearing Loss (i) Hearing Physiology

The defining event in the hearing process is the transduction of mechanical stimuli into electrical signals by hair cells, the sensory receptors of the internal ear. Stimulation results in the rapid opening of ionic channels in the mechanically sensitive organelles of these cells, their hair bundles. These transduction channels, which are non-selectively permeable, are directly excited by hair-bundle displacement.

The unique structural feature of the hair cell is the hair bundle, an assemblage of microscopic processes protruding from the cell's top or apical surface; when mechanically disturbed, the hair bundle remains relatively straight along its length but pivots about a flexible basal insertion. When the fluid moves in response to sound, the force of viscous drag bends the bundles, thereby initiating a response.

When the hair bundle is deflected, transduction channels open and positive ions, largely $K^+$, enter the cell. The depolarization evoked by this transduction current activates voltage-sensitive calcium channels. As $Ca^{2+}$ ions flow into the cell they augment depolarization and raise the intracellular concentration of $Ca^{2+}$, especially the local concentration just beneath the surface membrane. Elevated $Ca^{2+}$ concentrations activate $Ca^{2+}$-sensitive $K^+$ channels. As $K^+$ exits through these pores it initiates membrane repolarization and diminishes the activation of calcium channels. Once the membrane potential becomes more negative than its steady-state value, intracellular $Ca^{2+}$ concentration is reduced by sequestration of the ion within cytosolic organelles and by extrusion through $Mg^{2+}$-cofactored, ATPase-fueled ion pumps. The $Ca^{2+}$-sensitive $K^+$ channels have now closed and the hair cell returns to its initial condition.

(ii) Hearing Loss Pathophysiology

Hearing loss is a growing problem in an aging population and in occupational health: the latter particularly includes the military wherein about one-third of inductees have hearing loss by the end of basic training even when precautions have been taken. In a population-based study of 3,753 residents in Beaver Dam, Wisconsin, the prevalence of hearing loss in adults aged 48–92 years, was 45.9%. The average age of participants was 65.8 years. The hearing loss increased with age and was greater for men than women. The prevalence of hearing loss is a striking 95 percent in the 80+ age group. This translates into an increasingly serious problem in nursing homes.

Acute hearing loss may occur due to hair cell trauma from excessive $Ca^{2+}$ signaling or from the generation of reactive oxygen species (ROS) after noise exposure. Chronic progressive hearing loss is often associated with labyrinthine ischemia from either hematologic disturbances (e.g., increased blood viscosity, decreased red blood cell deformability) or from non-hematologic vasoconstriction due to progressive vascular endothelial dysfunction related to ROS.

Noise-induced trauma to the hair cells is sound-intensity dependent and can lead to hair cell death. Since mitotic hair cell replacement does not occur, traumatic hearing loss is permanent. The pathophysiology of traumatic hair cell loss is multivariable: hypoxia, excessive $Ca^{2+}$ signaling, vasoconstriction, intracellular energy exhaustion, ROS and excitotoxicity; each contribute individually and as a detrimental synergistic composite.

Shear stress is increased by vasoconstriction (inter alia) and increased shear stress raises calcium channel permeability as much as ten or twelve fold. Since $Ca^{2+}$ influx augments the ET-1 -induced vasoconstrictive effect of pooled intracellular $Ca^2$, a "circle-in-a-spiral" vasoconstrictive effect occurs.

α-lipoic acid (LA) spares the cochlear antioxidant defense system. Dose-dependent otoprotection is conferred by the antioxidant effect of LA against cisplatin ototoxicity. (Cisplatin initiates cochlear free-radical production which causes ototoxicity and depletes cochlear glutathione (GSH). These are prevented with LA administration.

LA can also improve hearing by upregulating mitochondrial function. Specific deletions within the mitochondrial DNA (mtDNA) occur with increasing frequency in hearing loss associated with aging (presbyacusis). These deletions are the result of chronic exposure to ROS. When sufficient mtDNA damage has accrued, the cell becomes bioenergetically deficient. The mtDNA deletions associated with aging and presbyacusis have been reduced in groups treated with LA in comparison with controls. LA may reduce age-associated deterioration in auditory sensitivity and improve cochlear finction, at least in part, due to its ability to protect and repair age-induced cochlear mtDNA damage, i.e., by upregulating mitochondrial fuiction.

Certain complexes of LA, particularly magnesium bis-α-lipoate and magnesium α-lipoate L-ascorbate appear not only to provide ROS defense, but also favorably to modulate $Ca^{2+}$ signaling and reduce production of the potent, long lasting vasoconstrictor,ET-1.

Enzymes involved in maintaining glutathione (gamma-glutamyl-cysteinyl-glycine (GSH in the reduced state) protect hair cells from ROS-induced damage, adding support to the findings that LA which protects or augments the GSH system in the cochlea can be protective against noise-induced hearing loss.

C. Insulin Resistance

Insulin resistance (IR) is prevalent in up to 35% of the population. It is most frequently a disorder of middle and later life. It is both a condition of the aging process and a process that advances aging; affecting in both processes, metabolism in totality: carbohydrate, lipid and protein.

Cellular resistance to the effectiveness of insulin (IR) results in above normal levels of insulin secretion. When this compensatory increase of insulin production cannot be maintained and/or when insulin resistance increases further, blood sugar rises, lipid and protein metabolism are disturbed even before a clinical diagnosis has been established, and insidious processes of vascular complications begin.

IR can lead to a congeries of pathologies other than hyperglycemia; most seriously, patients develop specific microvascular and non-specific macrovascular complications including retinopathy, nephropathy, neuropathy and frequently severe atherosclerosis affecting, among others, the coronary, cerebral and peripheral vascular trees. Causative mechanisms of these complications include free radical damage, nonenzymatic protein glycation, lipoprotein disturbances and disorders of sorbitol and myoinositol metabolism.

IR with secondary hyperinsulinemia and/or hyperglycemia contributes to many conditions associated with aging, e.g., hypertension, obesity, atherosclerosis, lenticular cataracts, lipid abnormalities and chronic metabolic perturbations including filly developed Type 2 diabetes.

In IR, as in aging, elevated circulating glucose reacts non-enzymatically with proteins and nucleic acids to form products that: 1) disturb the functionality of the cellular phospholipid membrane, 2) diminish tissue elasticity and 3) increase lipid peroxidation.

Disturbances in glucose/insulin metabolism are associated with greatly increased lipid peroxidation caused by elevated free radicals derived from the auto-oxidation of glucose. This augmented free radical formation and lipid peroxidation are associated with premature aging.

Ingestion of sugars, fats and sodium have been linked to decreased insulin sensitivity, while caloric restriction, exercise, ingestion of chromium, vanadium, magnesium, and certain antioxidants are putatively associated with greater insulin sensitivity. Thus, manipulation of the diet by influencing the glucose/insulin system may favorably affect lifespan and reduce the incidence of the microvascular and macrovascular complications stemming from IR.

The earliest rnicrovascular lesion relating to IR is thickening of the basement membrane. A healthy basement membrane provides stability and a permeability barrier. Cellular impermeability requires a negative electrical charge provided by heparan sulfate, a proteoglycan. Sulfate groups provided by thiol contributors like LA and N-acetylcysteine (NAC) appear to contribute to the adequacy of this necessary negativity of the cell membrane, perhaps by providing adequate stores of thiol groups required to maintain requisite levels of heparan sulfate. In diabetes both heparan sulfate levels and the basement membrane thickness are decreased. As a result, vessel permeability is increased. Increased vessel permeability is the most notable initial microvascular complication in patients whose IR leads to NIDDM.

In addition, arteriolar and capillary microvascular intraluminal pressure and flow are subject to nonlinear changes: laminar flow is further perturbed by clumping of cellular elements. These disturbances, plus the increased permeability of the basement membrane and associated vascular endothelial dysfunction, limit the normal vascular autoregulatory mechanisms, leading to clinically apparent microvascular and macrovascular insufficiencies of the legs, feet, heart, eye and brain.

D. Vasoconstriction

Vasoconstriction, or a reduction in the cross-sectional area of the lumen of blood vessels, is due either to vasospasm, inadequate vasodilatation, thickening of the vessel wall, or the accumulation of flow-restricting materials on the internal wall surfaces or within the wall itself. Vasoconstriction is a major factor in various diseases including progressive generalized atherogenesis, myocardial infarction, stroke, hypertension, glaucoma, migraine, hypertension and diabetes mellitus among others.

Vasoconstriction originates in a variety of ways. One example is the local conversion of circulating low-density lipoproteins (LDL) into oxidatively activated low-density lipoproteins (oxLDL), which are internalized via cellular macrophage scavenger receptors called "foam cells". These cells are bound to the vascular endothelium, release cytokines and trigger local expression of leukocyte adhesion molecules.

Another example is the unopposed endothelial cell release of the vasoconstrictor, ET-1. Prolonged vasospasm results in proliferation of vascular smooth muscle cells (VSMC) and a mechanical reduction of luminal cross-section. In particular, oxLDL and hyperlipidemia impair endothelial-dependent vascular relaxation because of the inhibition of the release of NO from endothelial cells. This induces a sometimes-inadequate adaptive increase in the level of intracellular GSH in vascular smooth muscle cells.

A third example is the free radical-stimulated activation, local accumulation, and adhesion of platelets and white blood cells on the endothelial surface which produce chemoattractants for macrophages that eventually will be converted into counterproductive "foam cells".

A fourth example is the irregular vasoconstriction or vascular aneurysmal pouching due to the death of perivascular pericytes in diabetes mellitus caused by the conversion of glucose to sorbitol.

Vasoconstriction and atherogenesis can be modulated by a number of mechanisms: inhibition of LDL oxidation by α-tocopherol (vitamin E) and ascorbate (vitamin C); limitation of the production of ROS and, thus, cell-mediated LDL oxidation; reduction of adhesion molecule expression and monocyte recruitment; protection of release of NO and reduction in the proliferation of VSMC, etc. Many, if not most, of these processes are regulated by nuclear factor-kappaB (NF-kappaB) or related transcription factors, which are redox-sensitive and capable of modification by antioxidants. Furthermore, antioxidants directly limit the cytotoxic effects of oxLDL and thereby reduce vascular cell necrosis and lesion progression.

II. Biofactors and Biochemistry

The main oxidizing free radicals (FR) are oxygen-derived metabolites: superoxide anion ($O^\bullet$), hydrogen peroxide ($H_2O_2$), hydroxyl radical ($OH^-$), hypochlorous acid (HOCl), chloramines ($NH_2Cl$), nitrogen oxides ($NO^\bullet$), ozone ($O_3$) and lipid peroxides. Living organisms produce these FR continually, either in the intracellular compartment by the mitochondrial respiratory chain and mixed function oxidase system, or in the extracellular compartment, especially by phagocytes. The body possesses complex protective antioxidant systems against this potentially toxic production, such as dismutase superoxides, catalases, metallic ion sequestration, enzymes which degrade proteins damaged by FR, metabolizing hydroperoxides, DNA repair processes, vitamins E, C and, in particular, the GSH enzyme system. A physiological steady state is established under normal conditions between the production of oxidants and their neutralization by antioxidants.

A. Glutathione (GSH)

Human GSH levels cannot be raised directly by supplemental administration in the diet. GSH is produced intracellular from the amino acids glutamic acid, cysteine and glycine and acts as a cofactor for protective enzymes such as selenium-dependent glutathione peroxidase (GSHPx. Zinc is a necessary trace element in its synthesis. GSH presence in the brain is enhanced by pineal melatonin via this neurohormone's ability to increase the mRNA of GSHPx. The important protective role of GSH in aging is firmly established.

Reduced GSH is necessary for intracellular transduction signaling, for the modulation of cellular apoptosis and necrosis, and the modulation of red blood cell fragility. These actions importantly protect vascular endothelium from free radical damage. GSH inhibits the peroxidation of LDL directly reducing atherosclerotic and vasoconstrictive risk, and oxLDL-induced mitochondrial DNA mutations. Besides their influence upon atherogenesis and vasoconstriction, these effects are linked to a variety of specific sensory neuropathies.

GSH plays multiple roles in the nervous system including free radical scavenging, redox modulation of ionotropic receptor activity, neurotransmission and resistance to glutamate-induced ROS. Evidence for these roles is present in Lou Gehrig's disease (ALS), Parkinson's disease and Alzheimer's disease. In addition, neurodegenerative disorders occurring with age, e.g. Alzheimer's disease and prion-based diseases like Creutzfeldt-Jakob disease are associated with a reduction of GSH levels. Normalization of the GSH level appears to exert a neuroprotective effect.

(i) Lipoic Acid (LA) and ROS

The proglutathione metabolic antioxidant LA (1,2-dithiolane-3-pentanoic acid) is a low molecular weight substance that occurs naturally in the R (+) configuration. It is absorbed from the diet, is both water- and lipid-soluble and crosses the blood-brain barrier. Within cells and tissues, the salt form (α-lipoate) is reduced to dihydrolipoate that is exported to the extracellular medium; hence, antioxidant protection is afforded to both intracellular and extracellular environments. LA acts as a mitochondrial coenzyme that is involved in reversing age-related declines in cellular $O_2$ consumption and impaired mitochondrial membrane potentials. It is important in decreasing malondialdehyde (MDA) levels (an indicator of lipid peroxidation) and in increasing ascorbic acid and GSH levels in rats, is a powerful scavenger of $O^\bullet$, $H_2O_2$, $OH^-$, HOCl, $NO^\bullet$ and lipid peroxides, and chelates a variety of metals, in particular $Fe^{3+}$. Since both the α-lipoate and dihydrolipoate forms have been shown to be potent antioxidants, both the oxidized and reduced forms of LA have antioxidant activity and either can regenerate through redox cycling other antioxidants like ascorbic acid and α-tocopherol, and raise intracellular GSH levels. LA can be directly administered as a dietary supplement, whereas GSH cannot. These various features suggest that LA may be useful in the treatment of glaucoma, ischemia-reperfusion injury, diabetes, neurodegenerative diseases, vasoconstriction and other pathologies associated with acute or chronic cellular oxidative damage.

FR generation is implicated in a variety of pathological processes including drug toxicity. For example, studies have shown that gentamicin increases the generation of ROS both in vivo and in vitro. In guinea pigs, LA has been shown to attenuate the cochlear damage induced by a regimen of aminoglycoside amikacinare compounds by inactivating ROS.

Experimental neurotoxicity in rat models can be induced by the intramuscular injection of mercuric chloride. Enhanced lipid peroxidation and perturbed antioxidant status are observed in the cerebral cortex, cerebellum and sciatic nerves of these rats. LA administered either as prophylactic or curative therapy has an ameliorating effect and improves nervous tissue antioxidant status.

(ii) GSH and LA

As a proglutathione entity, LA protects against oxidative damage in the heart (e.g., exercise-induced decreases in heart GSH S-transferase activity), liver and red muscle. Oral LA supplementation in rats increases levels of free LA in the gastrocnemius muscle and increases total GSH levels in the liver and blood.

After oxidative stress induced by hypoxia/reoxygenation, functional recovery of hypertrophied right rat heart may be insufficient because, in part, mitochondrial membrane potential does not recover sufficiently. Hearts treated with LA show significantly increased levels of adenosine 5'-triphosphate (ATP) and creatine phosphate content (as well as improvement in the ATP/ADP ratio) and a significantly higher content of oxidized GSH after reoxygenation. There is also distinct improvement of mitochondrial structure/function. This suggests a rational therapeutic combination with the FR scavenging properties of α-tocopherol.

Loss of GSH accompanied by concurrent mitochondrial dysfunction, can be inferred in vitro by losses of Complex I activity in male mouse brain slices and in vivo in selected regions of mouse CNS exposed to excitatory amino acids. The inhibition of Complex I is abolished by the maintenance of protein thiol homeostasis with pretreatment with GSH or with LA.

(iii) α-Lipoic Acid and NF-kappaB

Transcription factor NF-kappaB is a cell-signaling pathway. It leads, for example, to gene expression in keratinocytes after exposure to solar UV radiation (UVR). Exogenous supplementation of antioxidants prevents UVR-induced photo-oxidative damage. While high concentrations of NAC can inhibit NF-kappaB activation, low concentrations of LA have a similar significant effect. These results indicate that the very efficient antioxidant properties of LA may lie in its suppression of NF-kappaB activation.

Reduced GSH is a cofactor for the glyoxalase system, a metabolic pathway that catalyses the detoxification of α-oxoaldehydes (RCOCHO) to corresponding aldonic acids ($RCH(OH)CO_2H$). This protects cells from a-oxoaldehyde mediated formation of advanced glycation endproducts (AGE). AGE are implicated in a wide variety of diabetic vascular abnormalities and, perhaps, in the pathogenesis of macular degeneration. Studies have found that incubation of cultured bovine aortic endothelial cells (BAECs) with AGE albumin results in decreases of GSH and ascorbic acid levels. This increased cellular oxidative stress leads to the activation of NF-kappaB and promotes the upregulation of various NF-kappaB-controlled genes, including endothelial tissue factor. However, the addition of LA before AGE exposure completely prevents depletion of GSH and ascorbic acid by inhibiting the release and translocation of NF-kappaB from the endothelial cytoplasm into the nucleus. Because LA reduces this AGE-induced NF-kappaB mediated transcription, the expression of endothelial genes such as tissue factor and the vasoconstrictor ET-1 is reduced.

(iv) GSH, LA and Diabetes

As mentioned above, excessive oxidative stresses are associated with diabetic neuropathy. Increased ROS and concurrently decreased FR scavenger systems enhance multiple cytotoxic effects in diabetes. These elevated oxidative stresses and the subsequent activation of NF-kappaB have been linked to the development of many late diabetic complications, e.g., patients with diabetic nephropathy show higher NF-kappaB binding activity correlated with albuminuria-associated renal endothelial dysfimction. LA reduced the NF-kappaB binding activity and oxidative stress in associated ex vivo isolated peripheral blood mononuclear cells.

The administration of LA reduces the incidence of diabetic embryopathy in streptozocin-induced diabetic rats. In particular, the rate of neural tube defects in diabetic rats treated with LA during the organogenesis period of pregnancy is significantly reduced. In addition, accelerated atherogenesis within the placental vasculature in treated rats is absent from placentae obtained from LA-treated diabetic animals.

Elevated ROS contribute to many diabetic neurovascular deficits. The high level of ROS in diabetes mellitus is associated with impotence related to inadequate relaxation of the corpus cavernosum muscle in animal models and patients. In one study this deficit was prevented (93.9+/−7.1%) by administration of LA, and cavernosal relaxation returned to a nondiabetic range. These improvements may be related to reduced circulating ET-1 levels and an attenuation of induced vasoconstriction or smooth muscle cell contraction.

Elevated oxidative stress and impaired n-6 essential fatty acid metabolism contribute to defective diabetic nerve conduction velocity (NCV) and to nerve perfusion in diabetic rats. Racemate LA (racLA) produced improvement in laboratory trials. After 6 weeks of diabetes, 2 weeks of racLA treatment corrected 20% of sciatic motor and 14% of saphenous sensory NCV deficits. RacLA also corrected 49% of diabetic deficits in sciatic endoneural blood flow. In similar fashion, diabetic rats demonstrate depletion of neuropeptide Y-like immunoreactivity (NPYLI) in response to in vitro electrical stimulation of the dorsal root. Treatment with LA normalizes levels of NPYLI.

Importantly, LA has been found to increase peripheral glucose utilization in diabetic patients by inhibiting glucose production and gluconeogenesis. This may result from interference with hepatic fatty acid oxidation and from increased skeletal muscle GLUT4.

In the rat, diabetes-induced impairment of lens antioxidative defenses—e.g., disturbed glucose intermediary metabolism via glycolysis, impaired energy status and redox changes—are all partially prevented by LA. (However, sorbitol levels remained unaffected). These metabolic problems are coupled with a generally lower content of sulfhydryl proteins in the lens and vitreous of diabetics: dual failures that are associated with an increased formation of protein-bound free sulfhydryl radicals, one index of oxidative damage to proteins. In addition, GSHPx activity is decreased in the lenses of diabetic patients. The protective usefulness of GSH is preserved by the presence of LA.

FR have been proposed as fundamental to the development of diabetic retinopathy because they are routinely produced in high volume by the abnormal metabolism of diabetes. Microvascular ischemia/reperfusion cycles that interfere with or overwhelm the FR enzyme defense system of the retina, i.e., GSH and LA, are also implicated.

(v) GSH, LA and the Eye

LA administration increases lenticular levels of the thiol contributor, and GSH predecessor, cysteine. This is an important protection because the ciliary body in particular appears to contain an inducible and very active monooxygenase system prone to ROS generation. These ROS, combined with those produced via the cyclo-oxygenase pathway, probably result in damage through oxidative stress. Furthermore, in the retina the photoreceptor rhodopsin itself may be the photodynamic agent that initiates ROS formation. High concentrations of retinal polyunsaturated fatty acids (PUFAs) in the photoreceptor membranes form additional ROS by auto-oxidation. Retinal gammaglutamyl transpeptidase activity (GTT) and GSH levels are also significantly reduced in diabetic and galactosemic rats. Consumption of antioxidants such as ascorbic acid and α-tocopherol inhibits these decreases of retinal GTT activity and GSH levels, further suggesting that defects in GSH regulation in the diabetic retina are secondary to hyperglycemia-induced oxidative stress and would be amenable to betterment with an improvement in GSH availability.

Fatty acids, e.g., C22:6 omega 3, are especially concentrated in rods and cones and in the phosphatidyl ethanolamine of retinal synaptosomes. As a result of FR-induced peroxidation, malondialdehyde is formed. This aldehyde appears to cross-link the amino groups of proteins with phospholipids, which results in the production of retinal lipofuscin. From this source drusen are formed. These are precursors of senile macular degeneration—a major source of visual disability in the aging population.

The protective antioxidative capacity of the youthful and healthy ciliary body is fortunately very high (superoxide dismutase (SOD) and GSH). The peroxidation process in particular is countered by these enzyme systems and antioxidants. However, rapid oxidation of ascorbate in the aqueous yields $H_2O_2$, which is itself toxic to endothelial cells. This oxidation of ascorbate in the aqueous humor requires high levels of GSH. A potential, important relationship may exist between unmodulated aqueous increases of $H_2O_2$-derived toxic ROS (e.g., $OH^-$) and the development of various ocular pathologies such as glaucoma, cataract, macular degeneration and retinal vascular damage, including the neovascularization of prematurity.

The actions of LA as an antioxidant and as a preserver of GSH provide support for a use of LA in the reduction of cataract risk.

(vi) GSH, LA and Vasoconstriction

Redox-sensitive mechanisms are involved in VSMC growth. ROS that promote VSMC growth are inhibited by GSH and negatively influenced by LA.

Endothelial migration of monocytes is one of the first steps in atherogenesis. Monocyte-endothelial interactions are linked to the expression of adhesion molecules like vascular cell adhesion molecule-1 (VCAM-1). Stimulation of VCAM-1 by AGE has been demonstrated. Endothelial stimulation by AGE is followed by the generation of ROS and subsequent activation of NF-kappaB. (See further discussion, supra.) LA decreases the number and expression of VCAM-1 transcripts in AGE-stimulated cell cultures. As a result, pretreatment of endothelial cells with LA reduces AGE-induced endothelial binding of monocytes. This suggests that supplemental administration of LA will reduce AGE-albumin-induced endothelial expression of VCAM-1 and monocyte binding to endothelium.

Acute biliary obstruction is associated with the development of oxidative stress. Inflammatory F2-isoprostanes, formed during oxidant injury, are renal vasoconstrictors that act via thromboxane (TX)-like receptors. Administration of thiol-containing antioxidants, NAC and LA not only raises levels of protective hepatic GSH but also markedly and directly inhibits the formation of F2-isoprostane.

Because an inverse correlation exists between the extent of macrophage-mediated oxidation of LDL and cellular GSH content, supplemental thiols such as LA which increase GSH levels should protect endothelial cells from atherosclerotic damage, perturbations of laminar flow, VSMC hypertrophy, cell detachment, et al, and thus help to preserve a normal NO/ET-1 ratio.

Cellular oxygenases and antioxidants, including GSH, modulate macrophage-mediated oxidation of LDL in early atherogenesis. LA improves cellular GSH synthesis. Supplementation with LA should increase macrophage GSH content and GSHPx activity and reduce cellular oxLDL production.

Increased vascular oxidative stress, regardless of its source, impairs the effective vasorelaxive action of NO in atherosclerosis. NO action is improved by the administration of ascorbic acid (which regulates intracellular redox states) perhaps by sparing cellular GSH. By providing additional improvement in GSH synthesis and thus augmenting intracellular GSH, LA improves NO-dependent, flow-mediated dilation. 0

B. Magnesium ($Mg^{2+}$)

Although the recommended daily allowance of ionic $Mg^{2+}$ for humans is 350 mg. $Mg^{2+}$ deficiencies have been documented in many segments of the world population. The average adult in Western society has a dietary $Mg^{2+}$ shortfall of 90–178 mg. per day. $Mg^{2+}$ deficiencies are particularly prevalent among diabetics with normal renal function, alcoholics, smokers, the elderly, and those who suffer from a variety of gastrointestinal mobility disorders.

Ionic $Mg^{2+}$ in mammals resides in three compartments: (1) in bone; (2) in an intracellular bound form or in an intracellular unbound form; and (3) in circulating bound and unbound forms. When the concentration of circulating $Mg^{2+}$ in the bloodstream increases as a result of dietary uptake of $Mg^{2+}$, the body responds by attempting to sequester the $Mg^{2+}$ into one of the bound or intracellular forms listed above. However, if elemental $Mg^{2+}$ is rapidly ingested in a bulk amount that results in the absorption of a $Mg^{2+}$ bolus in excess of 8 mEq, the renal excretion of $Mg^{2+}$ quickly increases and becomes less efficient in the resorption of this element. Thus the accurate sustenance of an appropriate Mg level requires the repeated administration of carefully designed medicaments with correctly formulated, targeted amounts.

$Mg^{2+}$ deficiencies impair antioxidant defenses through decreased synthesis of GSH and a reduced activity of CuZnSOD. $Mg^{2+}$ deficiencies enhance general oxidative stress levels by raising circulating levels of factors that promote free radical generation and which are mitogenic. This may result in increased tissue necrosis in the presence of acute local levels of active oxygen species or hydroxyl radicals.

C. Copper ($Cu^{2+}$)

$Cu^{2+}$ is an essential trace element required for a number of enzymes that are necessary for normal metabolic function. Metabolic balance studies have demonstrated that daily $Cu^{2+}$ losses are approximately 1.3 mg/day. In order to remain in $Cu^{2+}$ balance, the average adult male must consume a diet that contains at least 2 mg copper/day. It has been assumed that most diets satisfy this requirement because of the ubiquitous presence of $Cu^{2+}$ in most foodstuffs. Recent studies, however, have shown that dietary $Cu^{2+}$ may often fall below the estimated daily needs.

The essential yet toxic nature of $Cu^{2+}$ demands tight regulation of the $Cu^{2+}$ homeostatic machinery to ensure that sufficient $Cu^{2+}$ is present in the cell to drive essential biochemical processes yet prevent accumulation to toxic levels.

The results of some studies demonstrate that $Cu^{2+}$ deficiency results in alterations of the regulatory mechanisms governing inflammation and thrombosis.

$Cu^{2+}$ is strongly involved in the synthesis of GSH and is necessary for the activity of the antioxidant CuZnSOD.

D. Zinc ($Zn^{2+}$)

Compared with controls, rats fed a $Zn^{2+}$-deficient diet without supplementary antioxidants have greater red blood cell osmotic fragility, higher concentrations of thiobarbituric acid-reactive substances (TBARS), higher GSHS-transferase activity, lower concentration of GSH and of GSHPx, as well as lower activity of CuZnSOD. However, high dietary levels of $Zn^{2+}$ can reduce levels of ZnCuSOD. In a separate study there was no relationship between serum $Zn^{2+}$ levels and CuZnSOD activity or the serum concentration of GSHPx activity in a group of healthy subjects. However in elderly subjects given supplements, mean plasma levels of α-tocopherol, vitamin C and $Cu^{2+}$ increased significantly after 6 months of supplementation and serum $Zn^{2+}$ after one year. A significant increase in GSHPx levels was observed in patients receiving these trace elements alone or in association with vitamins.

$Zn^{2+}$ binds the sulfhydryl groups in proteins, protecting them from oxidation. $Zn^{2+}$ status does not directly control tissue peroxide levels but can protect specific molecules against oxidative and peroxidative damage.

Many areas of the brain contain high contents of $Zn^{2+}$: the retina, the pineal gland (note relationship to the pineal antioxidant and neurohormone, melatonin) and the hippocampus all synthesize unique metallothioneins (MT) on a continuous basis. MT are $Zn^{2+}$-binding proteins consisting of 25–30% cysteine. GSH may participate in releasing $Zn^{2+}$ from MT. The concentration of $Zn^{2+}$ is altered in a number of disorders of the central nervous system: alcoholism, Alzheimer-type dementia, amyotrophic lateral sclerosis, Down's syndrome, epilepsy, Friedreich's ataxia, Guillaine-Barre syndrome, hepatic encephalopathy, multiple sclerosis, Parkinson's disease, Pick's disease, retinitis pigmentosa, retinal dystrophy, schizophrenia, and Wernicke-Korsakoff syndrome. Since several of these disorders—such as amyotrophic lateral sclerosis—are associated with oxidative stress and since MT are able to prevent the formation of free radicals, the induction of MT provides long-lasting protection to avert oxidative damage.

SUMMARY OF THE INVENTION

A. Metal Complexes of the Invention.

The metal complexes included in the invention may conform to either of the following formulae:

[A]M X wherein, a. A is α-lipoic acid (LA), b. M is $Mg^{2+}$, $Cu^{2+}$ or $Zn^{2+}$, and c. X is hydroxide, halide, acetate or ascorbate.

or

[A]$_2$M wherein, a. A is α-lipoic acid (LA), and b. M is $Mg^{2+}$, $Cu^{2+}$ or $Zn^{2+}$.

B. Synthesized in Accordance with this Invention are the Following Acid Salts:

EXAMPLE 1

Magnesium bis-α-Lipoate—Mg($C_8H_{13}O_2S_2$)$_2$

A solution of 10.23 g. of α-lipoic acid in 200 ml. of anhydrous ethanol was added with stirring to a solution of 2.86 g. of magnesium ethoxide (Aldrich Chemicals) in 100 ml. of anhydrous ethanol. The reaction mixture was stirred for 30 minutes and the solvent was then evaporated under reduced pressure. This afforded 10.8 g. of the magnesium salt of α-lipoic acid.

EXAMPLE 2

Zinc bis-α-Lipoate—Zn($C_8H_{13}O_2S_2$)$_2$

A suspension of 10.1 g of a-lipoic acid in 150 ml of methanol was treated dropwise with stirring with 100 ml of 0.5 N sodium hydroxide. After the addition was complete the reaction mixture was stirred for 15 min and then the solvents were evaporated under reduced pressure. The residue of the sodium salt was dissolved in 200 ml of water and treated with stirring with a solution of 3.1 g of zinc chloride in 50 ml of water. The volume of the resulting mixture was reduced by about 50% by evaporation under reduced pressure and the precipitate was collected by filtration, washed with water (2×50 ml) and vacuum dried to yield the zinc salt.

EXAMPLE 3

Copper bis-α-Lipoate—Cu($C_8H_{13}O_2S_2$)$_2$

To a suspension of 10 g of α-lipoic acid in 150 ml of methanol in a nitrogen atmosphere, was added with stirring a solution of 2.7 g of potassium hydroxide in 100 ml of water. The reaction mixture was stirred for 30 min and the solvents were evaporated under reduced pressure. The residue of the potassium salt was dissolved in 200 ml of water and treated, with stirring, under nitrogen with a solution of 5.9 g of cupric nitrate trihydrate in 50 ml of water. After 30 min the precipitate of copper bis-α-lipoate was collected by filtration, washed with cold water (2×50) and vacuum-dried at room temperature.

EXAMPLE 4

Magnesium α-Lipoate L-Ascorbate—Mg($C_8H_{13}O_2S_2$).($C_6H_7O_6$)

α-Lipoic acid (2 g) was dissolved in 50 ml of absolute alcohol and treated with a solution of 1.1 g of magnesium ethoxide (Aldrich Chemicals) in 10 ml of absolute alcohol. A solution of 1.8 g of L-ascorbic acid in 100 ml of absolute alcohol was next added and the reaction mixture was stirred for 30 min. The ethanol was evaporated under reduced pressure to give 3.9 g of the magnesium salt.

EXAMPLE 5

Zinc α-Lipoate L-Ascorbate—Zn($C_8H_{13}O_2S_2$).($C_6H_7O_6$)

To a stirred solution of 11.4 g of the sodium salt of α-lipoic acid (prepared according to example 2) and 9.9 g of sodium ascorbate in 300 ml of water is added 6.8 g of zinc chloride in 50 ml of water. The volume of the resulting mixture was reduced by about 50% by evaporation under reduced pressure and the precipitate was collected by filtration, washed with water (2×50) and vacuum-dried to give the zinc salt.

EXAMPLE 6

Copper α-Lipoate L-Ascorbate—Cu($C_8H_{13}O_2S_2$).($C_6H_7O_6$)

By repeating the procedure described in example 5 and replacing zinc chloride with cupric chloride, there is obtained the corresponding copper salt.

EXAMPLE 7

Magnesium α-Lipoate Acetate—Mg($C_8H_{13}O_2S_2$).($C_2H_3O_2$)

α-Lipoic acid (4 g) was dissolved in 100 ml of absolute alcohol and treated with a solution of 2.2 g of magnesium ethoxide in 15 ml of absolute alcohol. After 10 min 1.2 g of acetic acid was added and the solvent was evaporated under reduced pressure to give 5.5 g of the magnesium α-lipoate salt.

EXAMPLE 8

Magnesium α-Lipoate Hydroxide—Mg $(C_8H_{13}O_2S_2).(OH)$

By repeating the procedure of example 7 and replacing acetic acid with water, there is obtained the corresponding magnesium a-lipoate hydroxide.

EXAMPLE 9

Zinc α-Lipoate Chloride—Zn$(C_8H_{13}O_2S_2)$.(Cl)

To a stirred solution of 11.4 g of the sodium salt of a-lipoic acid (prepared according to example 2) was added a solution of 6.8 g of zinc chloride in 50 ml of water. After 30 min the volume of the reaction mixture was reduced by about 50% by evaporation under reduced pressure. The precipitate was filtered, washed with water (2×50 ml) and vacuum-dried to give the zinc chloride salt.

EXAMPLE 10

Copper α-Lipoate Chloride—Cu$(C_8H_{13}O_2S_2)$.(Cl)

By repeating the procedure of example 9 and replacing zinc chloride with cupric chloride there is obtained the copper chloride salt.

EXAMPLE 11

Copper α-Lipoate Acetate—Cu$(C_8H_{13}O_2S_2)$. $(C_2H_3O_2)$

A solution of 4.1 g of a-lipoic acid and 3.6 g of cupric acetate in 200 ml of ethanol was stirred un a nitrogen atmosphere for 1 hr. The solvent was evaporated under reduced pressure and the residual acetic acid was removed by heating the residue ant 40–50° c. in high vacuum (0.01 mm) for several hours. This gave 6.6 g of the copper salt as a powder.

EXAMPLE 12

(−) Enantiomers and d/l-Mixtures

The α-lipoic acid used in examples 1–11 is the naturally occurring (+) or R enantiomer (isomer). By repeating these examples with the (−) or S enantiomer or the d,l-mixture (+/− enantiomers) the salts of the corresponding (−) enantiomer and the d/l-mixture are obtained.

The invention resides in the presentation of processes for the synthesis and application of unique molecules presented in oral dosage forms for use as supplements in the clinical management of conditions and functions associated with chronic glaucoma, diabetes and insulin resistance, macular degeneration, lenticular cataract, atherosclerosis, essential hypertension, neurodegenerative diseases and vasoconstriction. It introduces a variety of molecules unique in design and/or in application.

GSH is a critically important antioxidant whose intracellular level must be maintained. These levels especially must be sustained at a high level in glaucoma, diabetes, macular degeneration and vasoconstriction. This invention provides clinically useful oral dosage forms of metal complexes derived from LA to ensure that appropriate levels of thiols, GSH and metallic biofactors that act in a complementary way are maintained in these clinical conditions.

Because GSH cannot be directly administered as a supplement in the human diet, the invention defines oral dosage forms of molecules that effectively will maintain in these disease states appropriate clinical levels of intracellular sulfhydryl groups in general and GSH in particular.

Magnesium, zinc and copper are necessary co-factors in multiple steps of cellular physiology and in maintaining among others: eukaryocyte membrane integrity, immune system stability, the synthesis of ASH, the activity of CuZnSOD, the activity of GSHPx, and the modulation of cellular calcium channel gating. All of these activities are impaired in the disease states described.

This invention defines and combines for use as dietary supplements, physiologically complementary proglutathiones and certain metallic complexes in: a) clinically effective and balanced formulations; b) clinically appropriate unit dosage forms; c) new therapeutic applications for each.

DETAILED DESCRIPTION OF THE INVENTION AND PREFERRED EMBODIMENTS

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, liquid solutions, ointments, creams, eye drops, suppositories, emulsions or suspensions. Management of the disease, condition or function may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological process or function in some manner. "Activity" is the ability to perform the function, or to induce or affect the process. Active agents and ingredients are distinguishable from excipients such as carriers, vehicles, diluents, lubricants, binders, buffers and other formulating aids, and encapsulating or otherwise protective components.

"Delivery vehicle" is a composition, which comprises one or more active agents, and is designed to release the active agent in a particular fashion, either by immediately dispersing the agents, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a fuction of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "substantially homogeneous," when used to describe a formulation (Or portion of a formulation) that contains a combination of components, means that the components, although each may be in particle or powder form, are fully mixed so that the individual components are not divided into discrete layers or form concentration gradients within the formulation.

Composition, Formulations and Dosages

Examples of divalent metal forms of la that can be used in this invention are magnesium lipoate, zinc lipoate and copper lipoate. Examples of other dosage forms are la ascorbate, magnesium α-lipoate ascorbate, zinc α-lipoate ascorbate, copper α-lipoate ascorbate and the bis forms of la.

In certain embodiments of the invention, the dosage form is a substantially homogeneous single layer tablet that releases all of its components into the stomach upon ingestion. In certain other embodiments of the invention, the dosage form is a tablet in which the active agents are protected by an acid-resistant coating for release only in the intestine, and optionally in a sustained-release manner over a period of time.

The dosage forms of this invention can be formulated for administration at rates of one or more unit dosage forms per day. Unit dosage forms to be taken three to four times per day for immediate release tablets are preferred. Unit dosage forms to be taken once or twice daily for controlled (sustained) release tablets are preferred.

The polymer matrix of the controlled (sustained) release tablet, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. The rate of diffusion the agent is reasonably constant for the useful life of the matrix (approximately four hours), by which time the incorporated agent is finally depleted and the matrix disintegrates. Such a single layer controlled release tablet, substantially homogenous in composition, is prepared as illustrated in the examples that follow.

The slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., USA; and the cellulose acetate pbthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of active agents to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

The amounts of the primary components of the oral dosage form of the pharmaceutical preparation of this invention can vary. Expressed in terms of milligrams per day some examples of components and preferred ranges are illustrated in the following Examples.

However, the following examples are used for illustrative purposes and do not encompass the entirety of the formulations contemplated by the invention, i.e., they are not intended to limit the variety of formulation combinations contemplated by the invention.

IMMEDIATE RELEASE

| | Magnesium α-Lipoate Compound | Magnesium | α-Lipoate |
|---|---|---|---|
| Ranges in milligrams per day | | | |
| Preferred | 87 | 3.6 | 60 |
| to | 1735 | 72 | 1200 |
| Most Preferred | 173 | 7 | 120 |
| to | 867 | 36 | 600 |

SINGLE LAYER UNIT DOSAGE FORM FOR: Magnesium α-Lipoate

| | | | Magnesium per day | |
|---|---|---|---|---|
| TABLET WEIGHT | tabs/day | mg/day | mg | mcg |
| 289 | 3.00 | 867 | | 36 |

FOR IMMEDIATE RELEASE IN THE STOMACH    100%

| | | % of formula | milligrams | Mag. α-Lipoate mg | mcg |
|---|---|---|---|---|---|
| $C_8H_{12}O_2S_2$ | Magnesium α-Lipoate | 73.28% | 635.69 | 600 | |
| | | | | excipients | |
| $Mg(C_{18}H_{35}O_2)_2$ | Magnesium Stearate | 0.78% | 6.78 | Mag Stearate 6.5 | |
| | Starch | 25.94% | 225.00 | Starch 225 (25%) | |

AQUEOUS FILM
SUSTAINED RELEASE

| | Magnesium α-Lipoate Compound | Magnesium | α-Lipoate |
|---|---|---|---|
| Ranges in milligrams per day | | | |
| Preferred | 81 | 3.6 | 60 |
| to | 1624 | 72 | 1200 |
| Most Preferred | 162 | 7 | 120 |
| to | 812 | 36 | 600 |

SINGLE LAYER UNIT DOSAGE FORM FOR: Magnesium α-Lipoate

| | | | Magnesium per day | |
|---|---|---|---|---|
| TABLET WEIGHT | tabs/day | mg/day | mg | mcg |
| 812 | 1.00 | 812 | | 36 |

FOR SUSTAINED RELEASE    100%

| | | % of formula | milligrams | mag α-Lipoate mg | mcg |
|---|---|---|---|---|---|
| $C_8H_{12}O_2S_2$ | Magnesium α-Lipoate | 78.29% | 635.69 | 600 | |
| | | | | excipients | |
| $Mg(C_{18}H_{35}O_2)_2$ | Magnesium Stearate | 0.77% | 6.26 | Mag Stearate 6.0 | |
| | Polymer ($H_2O$ Sol, Cellulose) | 20.94% | 170.00 | Polymer 170 (20%) | |

ACID RESISTANT FILM

IMMEDIATE RELEASE

| | Zinc α-Lipoate Compound | Zinc | α-Lipoate |
|---|---|---|---|
| Ranges in milligrams per day | | | |
| Preferred | 15 | 1.5 | 9 |
| to | 1230 | 125 | 781 |
| Most Preferred | 49 | 5 | 31 |
| to | 493 | 50 | 313 |

SINGLE LAYER UNIT DOSAGE FORM FOR: Zinc α-Lipoate

| | | | Zinc per day | |
|---|---|---|---|---|
| TABLET WEIGHT | tabs/day | mg/day | mg | mcg |
| 163 | 3.00 | 488 | | 50 |

FOR IMMEDIATE RELEASE IN THE STOMACH    100%

| | | % of formula | milligrams | Zinc α-Lipoate mg | mcg |
|---|---|---|---|---|---|
| $Zn(C_8H_{12}O_2S_2)$ | Zinc α-Lipoate | 73.65% | 359.61 | 310 | |
| | | | | excipients | |
| $Mg(C_{18}H_{35}O_2)_2$ | Magnesium Stearate | 0.75% | 3.65 | Mag Stearate 3.5 | |
| | Starch | 25.60% | 125.00 | Starch 125 | |

AQUEOUS FILM
SUSTAINED RELEASE

| | Zinc α-Lipoate Compound | Zinc | α-Lipoate |
|---|---|---|---|
| Ranges in milligrams per day | | | |
| Preferred | 14 | 1.5 | 9 |
| to | 1154 | 125 | 781 |
| Most Preferred | 46 | 5 | 31 |
| to | 463 | 50 | 313 |

-continued

SINGLE LAYER UNIT DOSAGE FORM FOR: Zinc α-Lipoate

| | TABLET WEIGHT 458 | tabs/day 1.00 % of formula | mg/day 458 milligrams | | Zinc per day mg 50 Zn α-Lipoate | mcg |
|---|---|---|---|---|---|---|
| $Zn(C_8H_{12}O_2S_2)_2$ | Zinc α-Lipoate | 78.51% | 359.61 | | 310 excipients | |
| $Mg(C_{18}H_{35}O_2)_2$ | Magnesium Stearate | 0.75% | 3.44 | Mag | Stearate 3.3 | |
| | Polymer ($H_2O$ Sol, Cellulose) ACID RESISTANT FILM | 20.74% | 95.00 | | Polymer 95 (20%) | |

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

We claim:

1. A method for the clinical management of a subject suffering from a condition selected from the group consisting of chronic essential hypertension, cerebral vascular disease, chronic open angle glaucoma, hearing loss, macular degeneration, lenticular cataract, insulin resistance, diabetic retinopathy, coronary artery disease, Parkinson's disease, Alzheimer's disease, neurodegenerative disease, and vasoconstriction, said method comprising administering to said subject an amount effective in reducing said condition of a metal α-lipoic acid complex of the formula

[A]M X wherein

A is α-lipoic acid,

M is a metal ion selected from the group consisting of $Mg^{+2}$, $Cu^{+2}$, and $Zn^{+2}$, and X is an anion selected from the group consisting of hydroxide, halide, acetate, ascorbate and bis-ascorbate.

2. A method for the clinical management of a subject suffering from a condition selected from the group consisting of chronic essential hypertension, cerebral vascular disease, chronic open angle glaucoma, hearing loss, macular degeneration, lenticular cataract, insulin resistance, diabetic retinopathy, coronary artery disease, Parkinson's disease, AlzheimeT's disease, neurodegenerative disease, and vasoconstriction, said method comprising administering to said subject an amount effective in reducing said condition of a metal α-lipoic acid complex of the formula $[A]_2$M X wherein A is α-lipoic acid, M is a metal ion selected from the group consisting of $Mg^{+2}$, $Cu^{+2}$, and $Zn^{+2}$, and X is an anion selected from the group consisting of hydroxide, halide, acetate, ascorbate and bis-ascorbate.

3. A process for the synthesis of magnesium bis-α-lipoate, said process comprising:
   (a) combining approximately 10.23 parts by weight of α-lipoic acid with approximately 200 parts by volume of anhydrous ethanol to form a first mixture;
   (b) stirring the first mixture into a solution formed by combining approximately 2.86 parts by weight of magnesium ethoxide with approximately 100 parts by volume of anhydrous ethanol to form a second mixture;
   (c) stirring the second mixture for approximately 30 minutes; and
   (d) evaporating solvent from the second mixture under reduced pressure to yield dry magnesium bis-α-lipoate salt.

4. A process for the synthesis of zinc bis-α-lipoate, said process comprising:
   (a) combining approximately 10.1 parts by weight of α-lipoic acid with approximately 150 parts by volume of methanol to form a suspension;
   (b) combining the suspension with approximately 100 parts by volume of approximately 0.5 N of sodium hydroxide added drop-by-drop to form a mixture;
   (c) stirring the mixture for approximately 15 minutes;
   (d) evaporating the mixture under reduced pressure to yield a dry residue;
   (e) dissolving the residue in approximately 200 parts per volume of water to form a solution;
   (f) combining the solution with a solution of approximately 3.1 parts per weight of zinc chloride combined with approximately 50 parts per volume of water to form a mixture of solutions;
   (g) evaporating solvent from the mixture of solutions to approximately 50% by volume under reduced pressure to form a partially reduced mixture;
   (h) filtering the partially reduced mixture to yield a precipitate;
   (i) washing the precipitate with approximately 100 parts per volume of water to form a filtrate; and
   (j) drying the filtrate in a vacuum to yield dry zinc bis-α-lipoate.

5. A process for the synthesis of magnesium α-lipoate L-ascorbate, said process comprising:
   (a) combining approximately 2 parts by weight of α-lipoic acid with approximately 50 parts by volume of absolute alcohol to form a solution;
   (b) combining the solution with a solution formed by combining approximately 1.1 parts by weight of magnesium ethoxide with approximately 10 parts by volume of absolute alcohol, to form a first mixture; and
   (c) combining the mixture with a solution formed by combining approximately 1.8 parts per weight of L-ascorbic acid with approximately 100 parts per volume of absolute alcohol to form a second mixture; and
   (d) stirring the second mixture for approximately 30 minutes; and
   (e) evaporating solvent from the second mixture under reduced pressure to yield dry magnesium a-lipoate L-ascorbate.

6. A process for the synthesis of copper bis-α-lipoate, said process comprising:
   (a) combining in a nitrogen atmosphere approximately 10 parts by weight of α-lipoic acid with approximately 150 parts by volume of methanol to form a suspension;
   (b) combining with stirring the suspension with a solution formed by combining approximately 2.7 parts by weight of potassium hydroxide with approximately 100 parts by volume of water to form a mixture;
   (c) stirring the mixture for approximately 30 minutes under reduced pressure to yield a residue;
   (d) dissolving the residue in approximately 200 parts per volume of water to form a solution;
   (e) combining with stirring for 30 minutes in a nitrogen atmosphere the solution formed by step (d) with a solution formed by combining approximately 5.9 parts per weight of cupric nitrate hydrate with approximately 50 parts per volume of water, to form a precipitate;
   (h) filtering the precipitate to form a filtrate;
   (i) washing the filtrate with approximately 100 parts per volume of cold water; and
   (j) drying the washed filtrate in a vacuum to yield dry copper bis-α-lipoate.

7. A process for the synthesis of zinc α-lipoate L-ascorbate, said process comprising:
   (a) combining approximately 10.1 parts by weight of α-lipoic acid with approximately 150 parts by volume of methanol to form a suspension;
   (b) combining the suspension with approximately 100 parts by volume of 0.5 N sodium hydroxide added drop-by-drop to form a first mixture;
   (c) stirring the first mixture for approximately 15 minutes;
   (d) evaporating the first mixture under reduced pressure to yield a residue;
   (e) combining approximately 11.4 parts per weight of the residue with approximately 9.9 parts per weight of sodium ascorbate to form a second mixture;
   (f) combining the second mixture with approximately 300 parts per volume of water to form a third mixture;
   (g) combining the third mixture with approximately 6.8 parts per weight of zinc chloride combined with approximately 50 parts per volume of water to form a fourth mixture;
   (h) reducing the fourth mixture by approximately 50% by volume by evaporation under reduced pressure to form a precipitate;
   (i) filtering the precipitate to form a filtrate; and
   (j) washing the filtrate with approximately 200 parts per volume of water; and
   (k) drying the washed filtrate under vacuum to yield dry zinc α-lipoate L-ascorbate.

8. A process for the synthesis of copper α-lipoate L-ascorbate, said process comprising:
   (a) combining approximately 10.1 parts by weight of α-lipoic acid with approximately 150 parts by volume of methanol to form a suspension;
   (b) combining the suspension with approximately 100 parts by volume of 0.5 N sodium hydroxide added drop-by-drop to form a first mixture;
   (c) stirring the first mixture for approximately 15 minutes;
   (d) evaporating the first mixture under reduced pressure to yield a residue;
   (e) combining approximately 11.4 parts per weight of the residue with approximately 9.9 parts per weight of sodium ascorbate to form a second mixture;
   (f) combining the second mixture with approximately 300 parts per volume of water to form a third mixture;
   (g) combining the third mixture with approximately 6.8 parts per weight of cupric chloride combined with approximately 50 parts per volume of water to form a fourth mixture;
   (h) reducing the fourth mixture by approximately 50% by volume by evaporation under reduced pressure to form a precipitate;
   (i) filtering the precipitate to form a filtrate; and
   (j) washing the filtrate with approximately 200 parts per volume of water; and
   (k) drying the washed filtrate under vacuum to yield dry copper α-lipoate L-ascorbate.

9. A process for the synthesis of magnesium α-lipoate acetate, said process comprising:
   (a) combining approximately 4 parts by weight of α-lipoic acid with approximately 100 parts by volume of absolute alcohol to form a solution;
   (b) stirring the solution into a solution formed by combining approximately 2.2 parts by weight of magnesium ethoxide with approximately 15 parts by volume of absolute alcohol to form a mixture of solutions;
   (c) stirring the mixture of solutions for approximately 10 minutes;
   (d) combining the mixture of solutions with approximately 1.2 parts by volume of acetic acid; and
   (e) evaporating the solvent under reduced pressure to yield dry magnesium α-lipoate acetate.

10. A process for the synthesis of magnesium α-lipoate hydroxide, said process comprising:
    (a) combining approximately 4 parts by weight of α-lipoic acid with approximately 100 parts by volume of absolute alcohol to form a solution;
    (b) stirring the solution into a solution formed by combining approximately 2.2 parts by weight of magnesium ethoxide with approximately 15 parts by volume of absolute alcohol to form a mixture of solutions;
    (c) stirring the mixture of solutions for approximately 10 minutes;
    (d) combining the mixture of solutions with approximately 1.2 parts by volume of water; and
    (e) evaporating solvent under reduced pressure to yield dry magnesium α-lipoate hydroxide.

11. A process for the synthesis of zinc α-lipoate chloride, said process comprising:
    (a) combining approximately 10.1 parts by weight of α-lipoic acid with approximately 150 parts by volume of methanol to form a suspension;
    (b) combining the suspension with approximately 100 parts per volume of 0.5 N sodium hydroxide added drop-by-drop;
    (c) stirring the product of step (b) for approximately 15 minutes to form a first mixture;
    (d) evaporating solvent from the first mixture under reduced pressure to yield a residue;
    (e) combining the residue with a solution prepared by combining approximately 6.8 parts by weight of zinc chloride with approximately 50 parts per volume of water to form a second mixture;
    (f) stirring the second mixture for approximately 30 minutes to form a precipitate;
    (g) evaporating solvent from the precipitate under reduced pressure until it is reduced by approximately 50 percent;

(h) filtering the precipitate to form a filtrate;

(i) washing the filtrate with approximately 200 parts per volume of water; and (j) drying the washed filtrate under vacuum to yield dry zinc α-lipoate chloride.

12. A process for the synthesis of copper bis-α-lipoate acetate, said process comprising:

(a) combining approximately 4.1 parts by weight of α-lipoic acid with approximately 3.6 parts by weight of cupric acetate to form a dry mixture;

(b) combining the dry mixture with approximately 200 parts by volume of ethanol to form a second mixture;

(c) stirring the second mixture for approximately one hour under a nitrogen atmosphere to form a residue; and (d) evaporating solvent from the residue by heating the residue at approximately 40–50° C. in a high vacuum (approximately 0.01 mmHg) for several hours to yield dry copper bis-α-lipoate acetate.

13. A process for the synthesis of copper α-lipoate chloride, said process comprising:

(a) combining approximately 10.1 parts by weight of α-lipoic acid with approximately 150 parts by volume of methanol to form a suspension;

(b) combining the suspension with approximately 100 parts per volume of 0.5 N sodium hydroxide added drop-by-drop;

(c) stirring the product of step (b) for approximately 15 minutes to form a first mixture;

(d) evaporating solvent from the first mixture under reduced pressure to yield a residue;

(e) combining the residue with a solution prepared by combining approximately 6.8 parts by weight of cupric chloride with approximately 50 parts per volume of water to form a second mixture;

(f) stirring the second mixture for approximately 30 minutes to form a precipitate;

(g) evaporating solvent from the precipitate under reduced pressure until it is reduced by approximately 50 percent;

(h) filtering the precipitate to form a filtrate;

(i) washing the filtrate with approximately 200 parts per volume of water; and (j) drying the washed filtrate under vacuum to yield dry copper α-lipoate chloride.

14. A process in accordance with claims 3, 4, 5, 6, 7, 8, 9, 10, or 11 for the synthesis of (–) S enantiomer forms, in which the α-lipoic acid is the (–) S enantiomer of α-lipoic acid to yield dry (–) S enantiomer forms of the α-lipoate complexes.

15. A process in accordance with claims 3, 4, 5, 6, 7, 8, 9, 10, or 11 for the synthesis of d,l (+/–) enantiomer forms, in which the α-lipoic acid is the d,l (+/–) enantiomer of α-lipoic acid to yield mixtures of dry d,l (+/–) enantiomer forms of the α-lipoate complexes.

\* \* \* \* \*